(12) United States Patent
Leussler et al.

(10) Patent No.: US 12,070,300 B2
(45) Date of Patent: Aug. 27, 2024

(54) AUTOMATIC POSITIONING OF ANTENNA CONNECTORS FOR MAGNETIC RESONANCE IMAGING

(71) Applicant: KONINKLIJKE PHILIPS N.V., Eindhoven (NL)

(72) Inventors: Christoph Leussler, Norderstedt (DE); Daniel Wirtz, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 993 days.

(21) Appl. No.: 17/046,109

(22) PCT Filed: Apr. 2, 2019

(86) PCT No.: PCT/EP2019/058264
§ 371 (c)(1),
(2) Date: Oct. 8, 2020

(87) PCT Pub. No.: WO2019/197215
PCT Pub. Date: Oct. 17, 2019

(65) Prior Publication Data
US 2021/0030306 A1 Feb. 4, 2021

(30) Foreign Application Priority Data
Apr. 9, 2018 (EP) .................... 18166265

(51) Int. Cl.
*A61B 5/055* (2006.01)
*G01R 33/28* (2006.01)
(Continued)

(52) U.S. Cl.
CPC ............ *A61B 5/055* (2013.01); *G01R 33/283* (2013.01); *G01R 33/34007* (2013.01); *G01R 33/3692* (2013.01)

(58) Field of Classification Search
CPC A61B 5/055; G01R 33/283; G01R 33/34007; G01R 33/3692
See application file for complete search history.

(56) References Cited

U.S. PATENT DOCUMENTS

| 5,065,760 | A | 11/1991 | Krause et al. |
| 7,970,452 | B2 | 6/2011 | Piron et al. |

(Continued)

FOREIGN PATENT DOCUMENTS

| CN | 203576502 U | 5/2014 |
| CN | 105629186 A | 6/2016 |

(Continued)

OTHER PUBLICATIONS

International Search Report and Written Opinion from PCT/EP2019/058264 mailed Jun. 28, 2019.

*Primary Examiner* — Sean A Frith

(57) ABSTRACT

The invention provides for a medical instrument (100, 400, 500, 600, 900, 1000, 1100. 1200, 1400) comprising a magnetic resonance imaging system. The medical instrument comprises: a radio frequency system (116) configured for sending and receiving radio frequency signals to acquire magnetic resonance imaging data (302). The radio frequency system is configured for connecting to a magnetic resonance imaging antenna (114). The medical instrument further comprises a subject support (120) configured for supporting at least a portion of a subject (118) in an imaging zone (108) of the magnetic resonance imaging system. The subject support comprises an antenna connector (124) configured for connecting to the magnetic resonance imaging antenna. The radiofrequency system is configured for connecting to the magnetic resonance imaging antenna via the antenna connector. The subject support comprises a remotely controllable actuator (126) configured for translating the antenna connector to a connector position (154, 126)

(Continued)

along a path (126). The medical instrument further comprises a memory (148) comprising machine executable instructions (150). The medical instrument further comprises a processor (144) for controlling the magnetic resonance imaging system. Execution of the machine executable instructions causes the processor to: receive (350) the connector position (154); and control (352) the remotely controllable actuator to move the antenna connector along the path to the connector position (128).

19 Claims, 14 Drawing Sheets

(51) Int. Cl.
　　　*G01R 33/34*　　　(2006.01)
　　　*G01R 33/36*　　　(2006.01)

(56) References Cited

U.S. PATENT DOCUMENTS

| | | | |
|---|---|---|---|
| 2007/0035301 A1* | 2/2007 | Nakabayashi | G01R 33/28 324/318 |
| 2010/0176800 A1* | 7/2010 | Biber | G01R 33/3642 324/207.13 |
| 2012/0059242 A1 | 3/2012 | Cauba et al. | |
| 2014/0218030 A1 | 8/2014 | Harvey | |
| 2015/0087966 A1* | 3/2015 | Anderson | A61B 5/055 600/415 |
| 2015/0268321 A1* | 9/2015 | Zhai | G01R 33/443 324/309 |
| 2016/0139218 A1 | 5/2016 | Possazini et al. | |
| 2016/0238677 A1* | 8/2016 | Fischer | A61B 5/055 |
| 2017/0003791 A1 | 1/2017 | Berget et al. | |
| 2017/0065830 A1* | 3/2017 | Vahala | G01R 33/4808 |
| 2017/0082716 A1* | 3/2017 | Greiser | G01R 33/5673 |
| 2017/0322271 A1* | 11/2017 | Gulaka | A61B 6/467 |
| 2017/0343626 A1* | 11/2017 | Tomiha | G01R 33/546 |
| 2018/0003791 A1 | 1/2018 | Kimmlingen et al. | |
| 2018/0313919 A1 | 11/2018 | Ortiz et al. | |

FOREIGN PATENT DOCUMENTS

| | | | | |
|---|---|---|---|---|
| JP | 2007068984 A | | 3/2007 | |
| WO | WO-2016034364 A1 | * | 3/2016 | A61B 5/055 |
| WO | WO-2016087272 A1 | * | 6/2016 | G01R 33/3415 |

\* cited by examiner

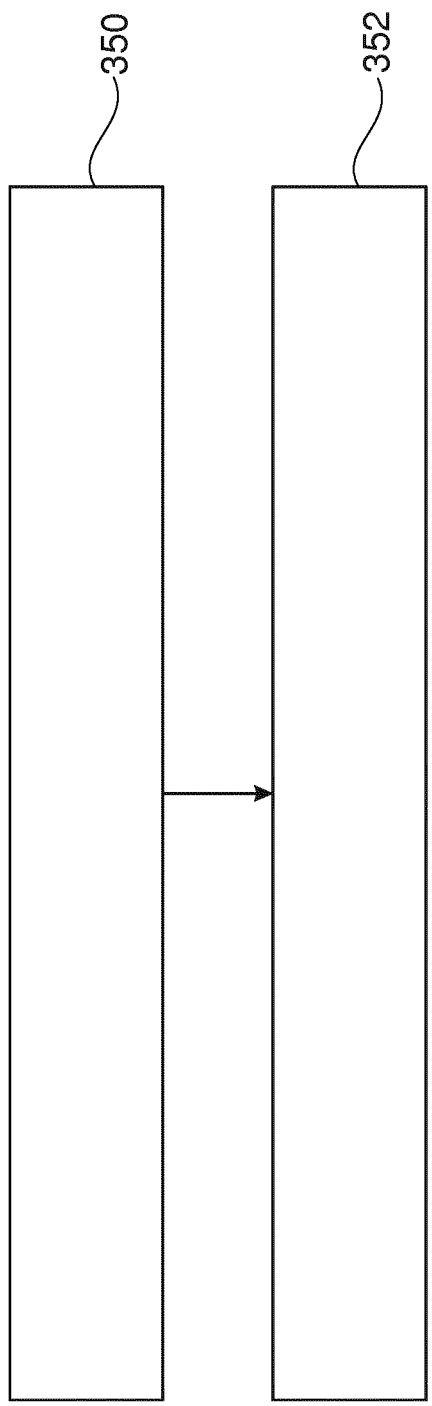

AUTOMATIC POSITIONING OF ANTENNA CONNECTORS FOR MAGNETIC RESONANCE IMAGING

CROSS REFERENCE TO RELATED APPLICATIONS

This application is a U.S. national phase application of International Application No. PCT/EP2019/058264 filed on Apr. 2, 2019, which claims the benefit of EP Application Serial No. 18166265.1 filed on Apr. 9, 2018 and is incorporated herein by reference.

FIELD OF THE INVENTION

The invention relates to magnetic resonance imaging, in particular to the radio-frequency systems of magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the BO field or the main magnetic field. The magnetic spins of material tend to align in the BO field. Radio frequency signals can be used to manipulate the orientation of the spins and cause them to precess which results in them emitting their own radio frequency signals. To send and receive these radio frequency signals magnetic resonance imaging antennas (or coils) are used. Large fixed coils may be used, or smaller coils which are placed on or about a subject may also be used.

United States patent application publication US 2017/0003791 discloses a patient couch for a magnetic resonance tomography system and a magnetic resonance tomography system are provided. The patient couch includes a feed facility for radiofrequency energy having a plurality of conduction paths for feeding radio frequency energy. The patient couch also includes a plurality of plug-in connectors for local coils having a transmit coil, and a distribution structure for the distribution of radio frequency energy from the feed facility to the plug-in connectors. The US patent application US2007/0035301 which discloses a coil support unit to an MRI apparatus. This known coil support includes a port to connect the RF coil to a signal cable. The port is slideable along the body axis of the top board (of the patient bed) by a moving unit to remain at the centre of the magnetic field.

SUMMARY OF THE INVENTION

The invention provides for a medical instrument, a computer program product, and a method in the independent claims. Embodiments are given in the dependent claims.

Embodiments may facilitate the use of magnetic resonance imaging antennas that can be placed on or about subjects by having a remotely controllable actuator that positions an antenna connector along a path of a subject support. A processor controlling a medical instrument that comprises a magnetic resonance imaging system receives a connector position and then controls the remotely controllable actuator to move the antenna connector to this connector position. This may provide several advantages. It may possibly reduce the chance that a magnetic resonance imaging antenna is used incorrectly. Positioning the antenna connector at a particular connector position may reduce the chance that a unskilled operator places the antenna incorrectly. It may also possibly provide for more convenient use of the magnetic resonance imaging antenna. The need for cable management may be reduced and placement of the antenna connector may in some examples be performed automatically.

In one aspect the invention provides for a medical instrument comprising a magnetic resonance imaging system. The medical instrument further comprises a radio-frequency system configured for acquiring magnetic resonance imaging data from an imaging zone of the magnetic resonance imaging system. The radio-frequency system is configured for sending and receiving radio-frequency signals to acquire magnetic resonance imaging data. The radio-frequency system is configured for connecting to a magnetic resonance imaging antenna. In some examples the magnetic resonance imaging antenna is a surface coil or other coil which may be attached or placed on a subject. The medical instrument further comprises a subject support configured for supporting at least a portion of the subject in an imaging zone of the magnetic resonance imaging system. The subject support comprises an antenna connector configured for connecting to the magnetic resonance imaging antenna. In some examples, the antenna connector may additionally provide connections for other devices such as, but is not limited to: ECG sensors, respiration sensors, motion sensor, patient feedback sensors, or others.

The radio-frequency system is configured for connecting to the magnetic resonance imaging antenna via the antenna connector. The subject support comprises a remotely controllable actuator configured for translating the antenna connector to a connector position along a path. The remotely controllable actuator may take different forms in different examples. For example, the remotely controllable actuator may be a system with pulleys, gears, stepper motors, pneumatics or hydraulics which is used to move the antenna connector along the path. The medical instrument further comprises a memory comprising machine-executable instructions. The medical instrument further comprises a processor for controlling the magnetic resonance imaging system. Execution of the machine-executable instructions causes the processor to receive a connector position. Execution of the machine-executable instructions further causes the processor to control the remotely controllable actuator to move the antenna connector along the path to the connector position.

This embodiment may be advantageous because a connector position can be chosen and then the remotely controllable actuator can be remotely moved to this position. This may enable a variety of things such as ensuring that the connector is placed in the optimal position with respect to the magnetic resonance imaging antenna. This for example may enable reducing the length of cables or connectors for the magnetic resonance imaging antenna, it may also help to eliminate the possibility of falsely placing the magnetic resonance imaging antenna or placing it in the wrong position.

In another embodiment the subject support comprises an NFC detector configured for receiving an NFC signal from the magnetic resonance imaging antenna. Execution of the machine-executable instructions further cause the processor to determine the connection position at least partially using the NFC signal. NFC stands for near field communication. This embodiment may be beneficial because it may enable an efficient and cost effective means of identifying the location of the magnetic resonance imaging antenna after it has been placed on or about a subject.

In another embodiment the magnetic resonance imaging antenna comprises an NFC transmitter and/or receiver that enables the NFC detector to pick up the NFC signal.

In another embodiment the medical instrument further comprises a camera configured for providing a camera image comprising the subject support and the position of the patient on the support. Execution of the machine-executable instructions further causes the processor to determine the connector position using the camera image. This embodiment may be beneficial because it provides a means for determining the connector position using a contactless means.

In another embodiment the processor is configured for registering an antenna location model to the camera image. For example, if a surface coil or other coil has been placed on or about the subject the antenna location model may be used to determine the location of the magnetic resonance imaging antenna. The determination of the connector position using the camera image is at least partially performed using the registration of the antenna location model. For example, the antenna location model may have a mapping that indicates what the connector position should be for various positions of the magnetic resonance imaging antenna. The antenna location model may be used to locate the magnetic resonance imaging antenna in the image and then determine the location of the magnetic resonance imaging antenna.

In another embodiment, the processor is configured for registering a subject model to the camera image. The determination of the connector position using the camera image is at least partially performed using the registration of the subject model. In this example the camera may be used to detect a subject who is placed on the subject support. The subject model may then be registered and the location of the subject is then known with respect to the subject support. This may be used for determining the connector position before the magnetic resonance imaging antenna has been place on or about the subject. This may be beneficial because it may enable placing the connector position in a location which helps the operator to place the magnetic resonance imaging antenna in the correct position. For example, if the magnetic resonance imaging antenna has a short cable the pre-placement of the connector position may eliminate the possibility of placing the magnetic resonance imaging antenna in a false position.

In another embodiment execution of the machine-executable instructions further cause the processor to receive a magnetic resonance imaging region of interest selection. The connector position is at least partially determined using the MRI region of interest selection and the registration of the subject model. For example, for a particular location of the subject the MRI region of interest can be superimposed on the registered subject model. This can then be used to infer where the magnetic resonance imaging antenna can be placed. This may further aid in placing the magnetic resonance imaging antenna properly on a subject.

In another embodiment the subject support further comprises a linear position selector distributed along the path. Execution of the machine-executable instructions further cause the processor to receive a selected location from the linear position selector. The connector position is at least partially determined using the selected position. This embodiment may be beneficial because the operator can indicate where a preferred location of the antenna connector is.

In another embodiment the linear position selector is a linear array of buttons. This is a collection of buttons located along the path one after the other and pushing one of the buttons indicates a possible or preferred connector position. The linear array of buttons may also be known by the term as a radio buttons.

In another embodiment the linear position selector is a touch sensor. For example, there may be one or more touch sensors distributed along the path and the operator need only touch the touch sensor in the appropriate location to indicate the connector position.

In another embodiment the medical instrument further comprises a radiotherapy system configured for irradiating a target zone. The target zone is within the imaging zone. Execution of the machine-executable instructions further cause the processor to receive radiotherapy instructions configured for controlling the radiotherapy system to irradiate the target zone. Execution of the machine-executable instructions further cause the processor to determine a beam path using the radiotherapy instructions. Execution of the machine-executable instructions further cause the processor to modify the connector position to avoid the beam path. Execution of the machine-executable instructions further cause the processor to control the radiotherapy system to irradiate the target zone using the radiotherapy instructions. This embodiment may be beneficial because it may provide for a means to help improve the quality of the radiotherapy.

During the radiotherapy a magnetic resonance image acquired by the magnetic resonance imaging system may be used to guide the radiotherapy. The magnetic resonance imaging may also be used to register the radiotherapy instructions to the position of the subject.

The radiotherapy system may for example be a LINAC system, a gamma ray system, an X-ray beam system, or other radiotherapy system. In some examples, the radiotherapy system may also be a nuclear medical imaging system. For example a radiological source or tracer has been placed in the target zone. The beam path can be radiation emitted by the radiological source or tracer and the antenna connector can then be placed to reduce obstruction of the emitted radiation. Nuclear medical imaging systems may include positron emission tomography (PET) systems and single photon emission computed tomography (SPECT).

In another embodiment the medical instrument comprises the magnetic resonance imaging antenna.

In another embodiment the magnetic resonance imaging antenna comprises an RF cable with an antenna plug. The antenna plug is configured for coupling with the antenna connector. The antenna plug comprises any one of the following: an MRI antenna preamplifier, a digital-to-analogue converter, an analogue-to-digital converter, and combinations thereof. This may be beneficial because the components of the magnetic resonance imaging antenna which may add bulk and weight to the antenna are moved to the antenna plug.

The antenna connector may provide a standard interface for using with the antenna plug, for example it may provide DC power and a digital transmission path. For example, the antenna plug may communicate with the rest of the magnetic resonance imaging system via an optical digital telecommunication path or a wireless one. The antenna connector may also provide a DC power for powering the various electronic components contained within the antenna plug.

In another embodiment the radio-frequency system comprises coil electronics within the subject support. The coil electronics are configured to move with the antenna connector. The coil electronics comprise any one of the following: an MRI antenna preamplifier, a digital-to-analogue converter, an analogue-to-digital converter, and combinations thereof. In this embodiment the active components which are typically placed on a magnetic resonance imaging antenna are placed within the subject support. This may be enabled by the fact that the moving connector enables a very short cable to be used.

In another embodiment the antenna connector comprises an RF system transceiver configured for forming a wireless connection with the magnetic resonance imaging antenna. Execution of the machine-executable instructions further cause the processor to determine a location of the magnetic resonance imaging antenna at least partially using the RF system transceiver. Execution of the machine-executable instructions further cause the processor to determine the connector location using the location of the magnetic resonance imaging antenna. This embodiment may be beneficial because it may provide for a cost effective means of implementing the automatic connector positioning.

In another embodiment the medical instrument further comprises the magnetic resonance imaging antenna. The magnetic resonance imaging antenna further comprises an antenna transceiver configured for forming the wireless connection with the RF system transceiver. The antenna transceiver could provide a localization by signal strength as the antenna connector is moved or for example by functioning as a transponder.

The magnetic resonance imaging antenna in this embodiment could for example have a battery. In this case the magnetic resonance antenna may comprise the analog to digital, digital to analog converter and/or preamplifier.

In another embodiment the subject support is detachable from the magnetic resonance imaging system.

In another embodiment the memory further contains pulse sequence instructions configured for acquiring magnetic resonance imaging data according to a magnetic resonance imaging protocol. Execution of the machine-executable instructions further cause the processor to control the magnetic resonance imaging system with the pulse sequence commands to acquire the magnetic resonance imaging data. Execution of the machine-executable instructions further cause the processor to reconstruct a magnetic resonance image from the magnetic resonance imaging data.

In another embodiment the connection between the magnetic resonance imaging antenna and the magnetic resonance imaging system comprises an optical connection.

In another aspect the invention provides for a method of operating the medical instrument. The medical instrument comprises a magnetic resonance imaging system. The medical instrument further comprises a radio-frequency system configured for acquiring magnetic resonance imaging data from an imaging zone of the magnetic resonance imaging system. The radio-frequency system is configured for sending and receiving radio-frequency signals to acquire the magnetic resonance imaging data. The radio-frequency system is configured for connecting to a magnetic resonance imaging antenna. The medical instrument further comprises a subject support configured for supporting at least a portion of a subject in an imaging zone of the magnetic resonance imaging system.

The subject support comprises an antenna connector configured for connecting to the magnetic resonance imaging antenna. The radio-frequency system is configured for connecting to the magnetic resonance imaging antenna via the antenna connector. The subject support comprises a remotely controllable actuator configured for translating the antenna connector to a connector position along a path. The method comprises receiving a connector position. The method further comprises controlling the remotely controllable actuator to move the antenna connector along the path to the connector position.

In another embodiment the path is a linear path.

In another embodiment the path is aligned with a z-axis of a magnet of the magnetic resonance imaging system.

In another embodiment at least a portion of the path follows a curve. This may be beneficial when connecting a head coil or other coil dedicated to a particular anatomical region.

In another embodiment a first portion of the path follows the z-axis and at least a second portion of the path moves perpendicular to the z-axis. This may be beneficial when connecting a head coil or other coil dedicated to a particular anatomical region.

In another aspect the invention provides for a computer program product comprising machine-executable instructions for execution by a processor controlling a medical instrument. The medical instrument comprises a magnetic resonance imaging system. The medical instrument further comprises a radio-frequency system configured for acquiring magnetic resonance imaging data from an imaging zone of the magnetic resonance imaging system. The radio-frequency system is configured for sending and receiving radio-frequency signals to acquire the magnetic resonance imaging data. The radio-frequency system is configured for connecting to a magnetic resonance imaging antenna.

The medical instrument further comprises a subject support configured for supporting at least a portion of a subject in an imaging zone of the magnetic resonance imaging system. The subject support comprises an antenna connector configured for connecting to the magnetic resonance imaging antenna via the antenna connector. The subject support comprises a remotely controllable actuator configured for translating the antenna connector to a connector position along a path. Execution of the machine-executable instructions causes the processor to receive a connector position. Execution of the machine-executable instructions further causes the processor to control the remotely controllable actuator to move the antenna connector along the path to the connector position.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which:

FIG. 3A shows a flow chart which illustrates a method of operating the medical instrument of FIG. 1;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
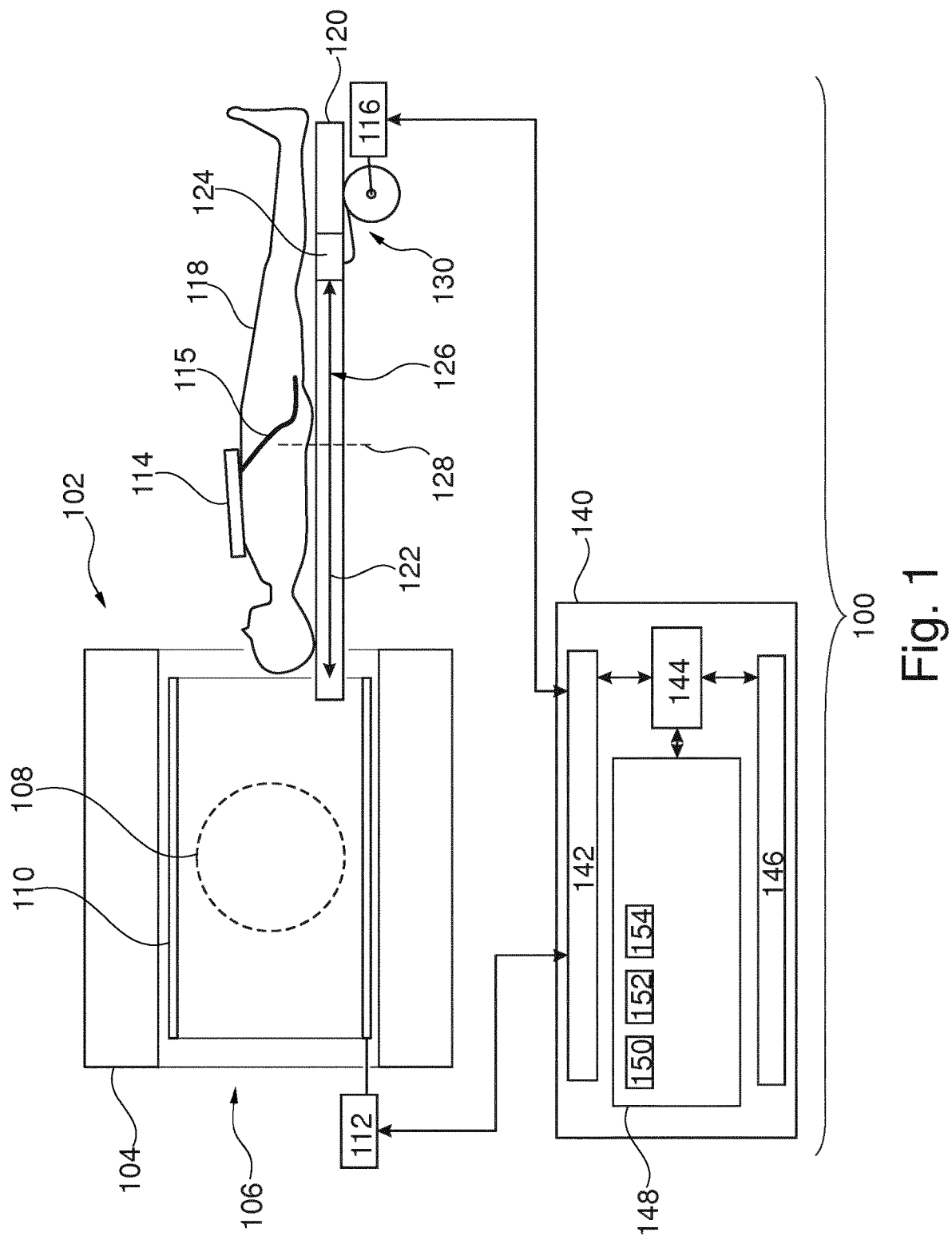
FIG. 1 illustrates an example of a medical instrument.

FIG. 1 illustrates an example of a medical imaging system 100. The medical imaging system 100 comprises a magnetic resonance imaging system 102. The magnetic resonance imaging system 102 comprises a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance data that is acquired typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a magnetic resonance imaging antenna 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel, coil, or antenna. The magnetic resonance imaging antenna 114 is connected to a radio frequency system 116. In some cases the radio frequency system 116 may be a transceiver that connects with a magnetic resonance imaging antenna 114. In other cases the radio frequency system 116 may be a system that controls and/or communicates with a preamplifier, transmitter, and/or receiver on the magnetic resonance imaging coil.

The magnetic resonance imaging antenna 114 and radio frequency system 116 may be replaced by separate transmit and receive coils and a separate transmitter and receiver. It is understood that the magnetic resonance imaging antenna 114 and the radio frequency system 116 are representative. The magnetic resonance imaging antenna 114 and the radio frequency system 116 may have multiple receive/transmit channels. For example if a parallel imaging technique such as SENSE is performed, the magnetic resonance imaging antenna could 114 will have multiple coil elements.

The subject support 120 is configured for supporting the subject 118 at least partially within the imaging zone 108. The subject support 120 is shown as having been withdrawn or not been placed yet into the bore 106 of the magnet 104. The subject support 120 comprises an antenna connector 124 that can be moved along a path 126 by a remotely controllable actuator 122. The arrow 122 indicates both an actuator and the path 126 that it can make the antenna connector 124 travel. The magnetic resonance imaging antenna 114 has a cable 115 that can be connected to the antenna connector 124. In this example the cable 115 is relatively short so the antenna connector 124 needs to be optimally moved to the physical location 128 of a connector position. In this example the transceiver 116 is connected to the antenna connector 124 using a cable management system 130. In different examples the cable 115 could take different forms. In some forms the cable 115 is a radio-frequency cable. In other examples the cable may also include optical or other digital transmission elements. In yet other examples the cable 115 may be replaced with a wireless connection.

The radio frequency system 116 and the gradient controller 112 are shown as being connected to a hardware interface 142 of a computer system 140. The computer system further comprises a processor 144 that is in communication with the hardware interface 142, a memory 148, and a user interface 146. The memory 148 may be any combination of memory which is accessible to the processor 144. This may include such things as main memory, cached memory, and also non-volatile memory such as flash RAM, hard drives, or other storage devices. In some examples the memory 148 may be considered to be a non-transitory computer-readable medium.

The memory 148 is shown as containing machine-executable instructions 150. The machine-executable instructions 150 enable the processor 144 to control the operation and function of the medical instrument 100. The machine-executable instructions 150 may also enable the processor 144 to perform various data analysis and calculation functions. The computer memory 148 could also containing pulse sequence commands. The pulse sequence commands could be configured for controlling the magnetic resonance imaging system 102 to acquire magnetic resonance imaging data from the subject 118 according to a magnetic resonance imaging protocol.

The memory 148 is further shown as containing a connector position 154 that has been received by the computer system 140. The connector position 154 corresponds to the physical location 128. The processor 144 can then control the actuator 122 to move the antenna connector 124 to the physical location 128.

Figure 2:
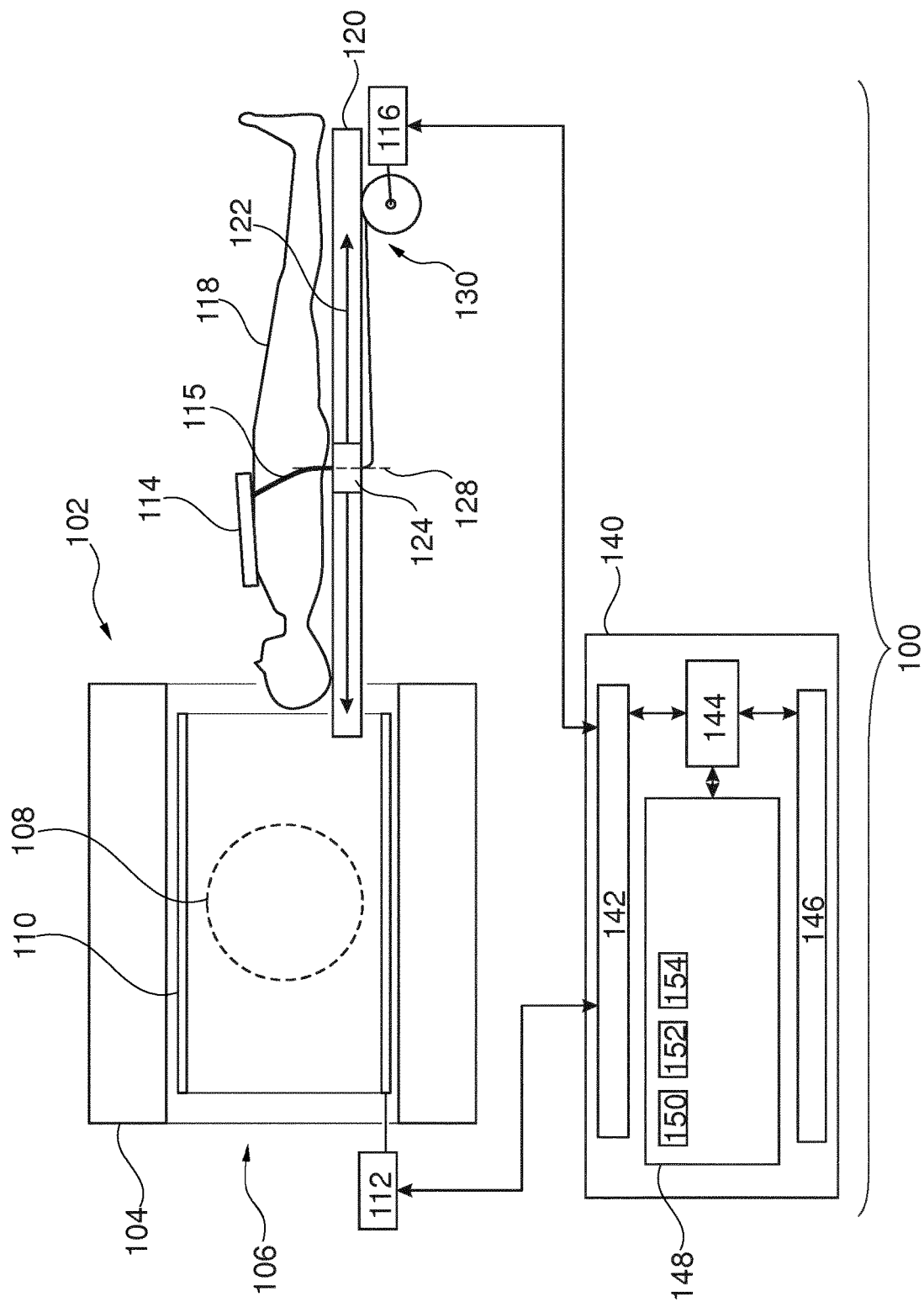
FIG. 2 shows a further view of the medical instrument of FIG. 1.

FIG. 2 shows a further view of the medical instrument 100. In the view shown in FIG. 2 the actuator 122 has been used to move the antenna connector 124 to the connector position 128. This has brought the antenna connector 124 close enough that the cable 115 could be connected to the antenna connector 124. The magnetic resonance imaging antenna 114 is now able to be used.

Figure 3:
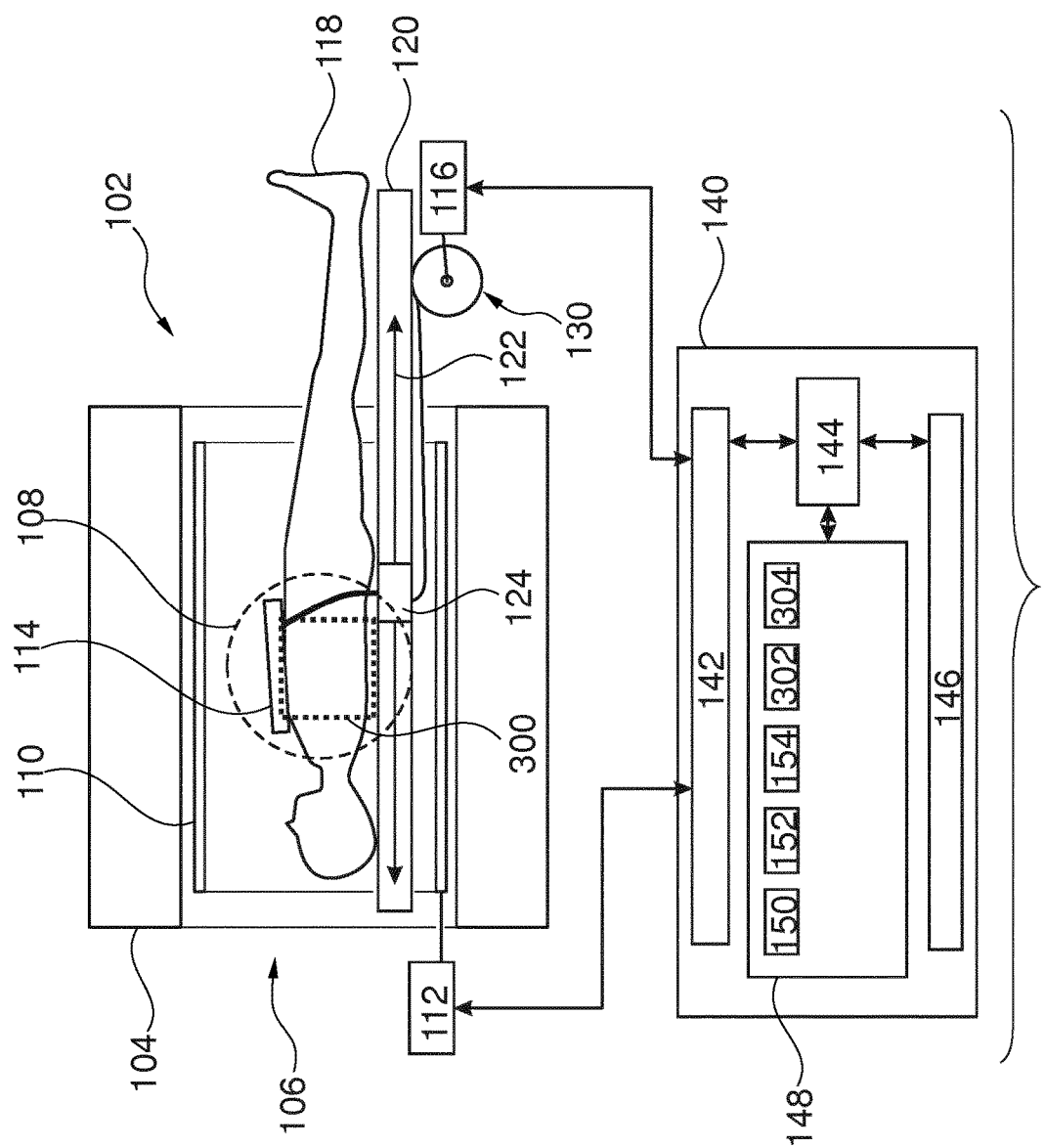
FIG. 3 shows a further view of the medical instrument of FIG. 1.

FIG. 3 shows a further view of the medical imaging system 100. In this example the subject support 120 has been moved into the bore 106 of the magnet 104. The subject 118 is now positioned such that the magnetic resonance imaging antenna 114 is within the imaging zone 108 and is able to image a region of interest 300.

The computer memory 148 is further shown as containing magnetic resonance imaging data 302 that has been acquired from the imaging zone 300 by controlling the magnetic resonance imaging system 102 with the pulse sequence commands 152. The memory 148 is further shown as containing a magnetic resonance image 304 that has been reconstructed from the magnetic resonance imaging data 302.

FIG. 3A shows a flowchart which illustrates a method of operating the medical imaging system 100 illustrated in FIGS. 1, 2 and 3. First in step 350 the connector position 154 is received. Next in step 352 the remotely controllable actuator 122 is controlled to move the connector 124 to the connector position 128.

In FIGS. 1, 2 and 3 the connector position 154 is shown as being in the memory 148. FIGS. 4-8 illustrate additions that can be made to the medical imaging system 100 such that the connector position 154 is either received manually from the operator or is obtained automatically. The examples shown in FIGS. 4-8 may be freely combined with the example illustrated in FIGS. 1-3.

Figure 4:
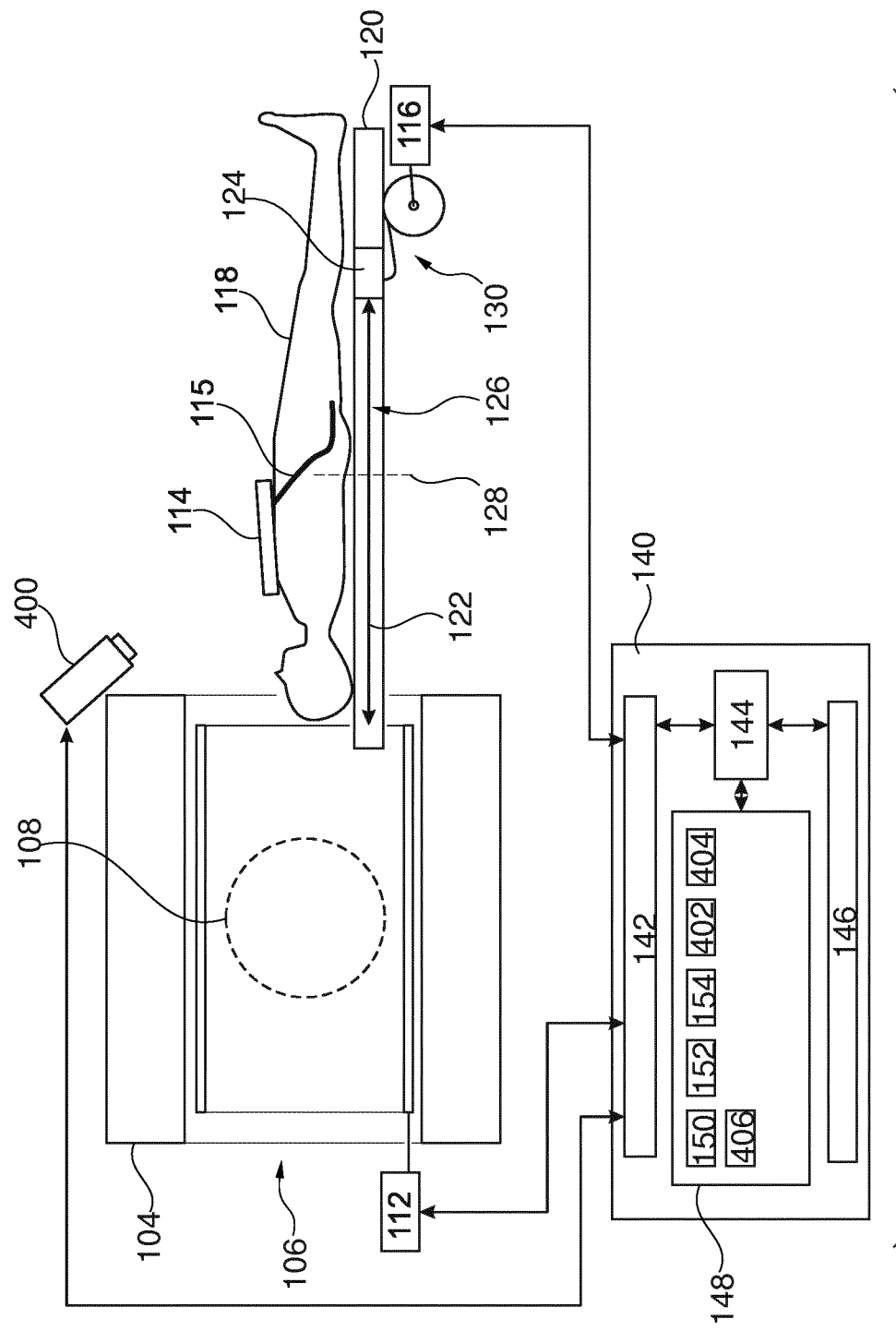
FIG. 4 illustrates a further example of a medical instrument.

FIG. 4 shows a further example of a medical imaging system 400. The medical imaging system 400 of FIG. 4 is similar to the medical imaging system 100 of FIGS. 1-3 except there is an additional camera system 400. The camera system 400 may be formed by one or more cameras. The one or more cameras may be inside and/or outside of the bore 106 of the magnet 104. The camera system is pointed at and is able to image a surface of the subject support 120.

The memory 148 is further shown as containing a camera image 402 acquired using the camera system 400. The image 402 shows an image of the magnetic resonance imaging antenna 114 on the subject 118. The memory 148 is further shown as containing an antenna location model 404. The memory 148 is further shown as containing a registration 406 of the antenna location model 404 to the camera image 402. The registration 406 is equivalent to knowing the location of the magnetic resonance imaging antenna 114. The registration 406 may then be used to compute the connector position 154.

The connector position 154 may for example be part of the antenna location model 404 or there may be a look-up table or other data which can be used to infer or calculate the position of the connector position 154. The medical imaging system 400 of FIG. 4 is able to automatically detect the location of the magnetic resonance imaging antenna 114 and move the antenna connector 124 to the proper location.

Figure 5:
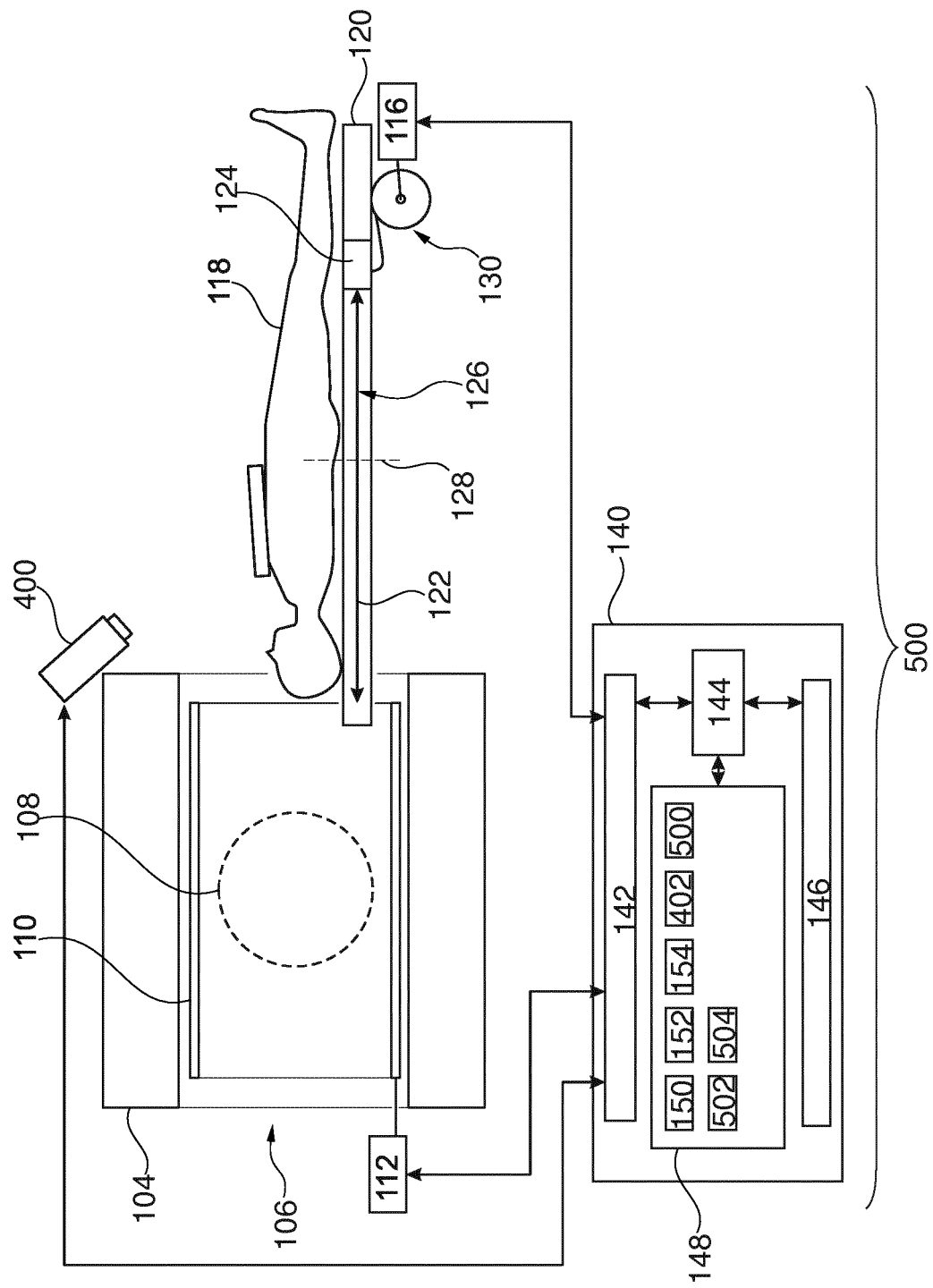
FIG. 5 illustrates a further example of a medical instrument.

FIG. 5 illustrates a further example of a medical imaging system 500. The medical imaging system 500 in FIG. 5 is similar to that depicted in FIG. 4. The medical imaging system 500 still comprises the camera system 400. However, as is noted in FIG. 5, the magnetic resonance imaging antenna has not yet been placed on the subject 118. The memory 148 is further shown as containing the camera image 402. However, in this example the camera image 402 only contains an image of the subject 118 reposing on the subject support 120.

The memory 148 is further shown as containing a subject model 500. The memory 148 is further shown as containing a registration 502 of the subject model 500 to the camera image 402. This is equivalent to indicating the position of the subject 118. The registration 502 may then be used to compute the connector position 154. The memory 148 is further shown as containing an optional MRI region of interest selection 504. This for example may be a region of interest relative to the subject model 500. This may then be used to locate a desired region of interest to be imaged in the actual subject 118. The MRI region of interest selection 504 and the registration 502 may also be used to compute the connector position 154.

Figure 6:
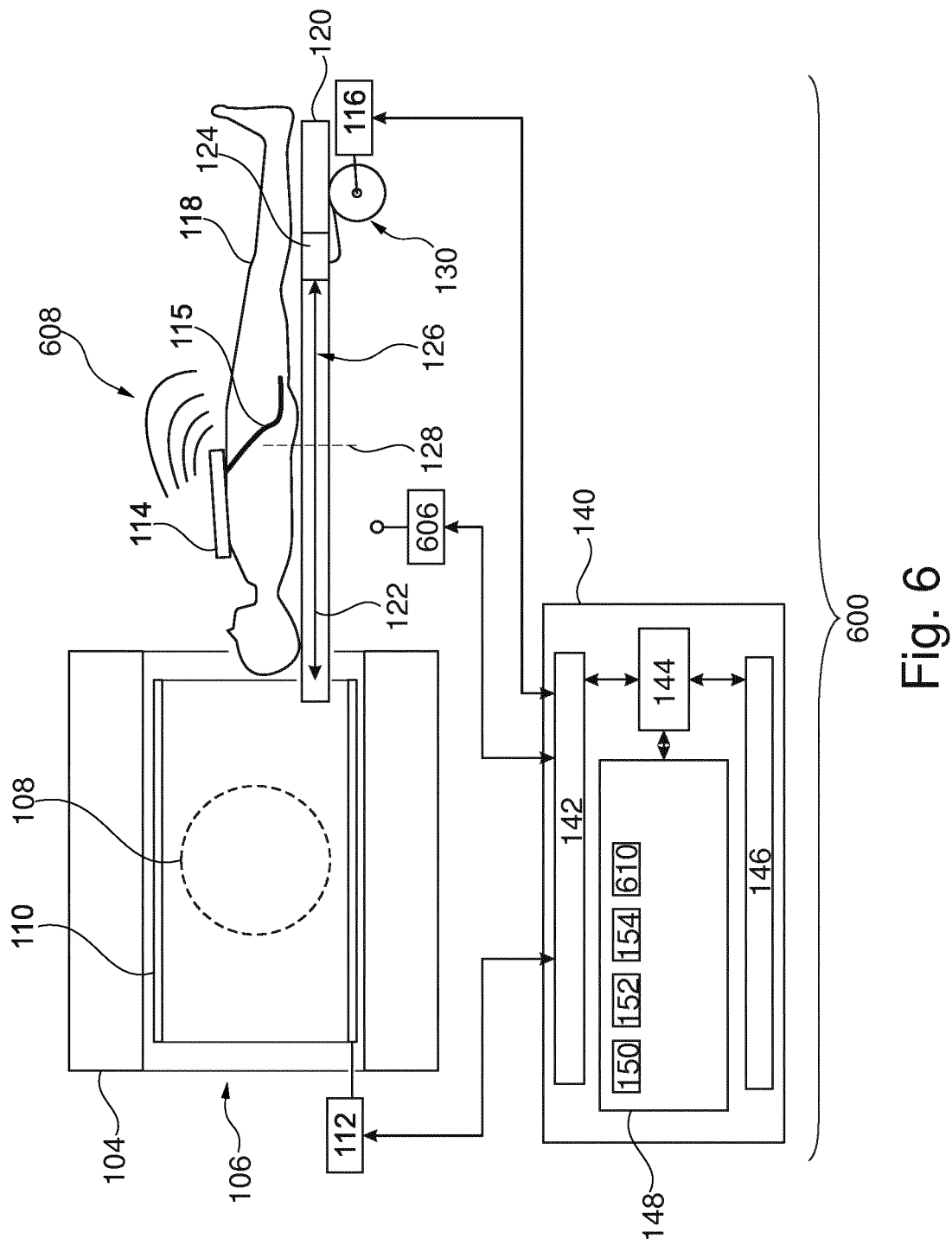
FIG. 6 illustrates a further example of a medical instrument.

FIG. 6 illustrates a further example of a medical imaging system 600. The example illustrated in FIG. 6 is similar to that illustrated in FIGS. 1-3. The medical instrument 600 in FIG. 6 is shown as additionally comprising a near field communication or NFC detector 606. The magnetic resonance imaging antenna 114 comprises an NFC transmitter or transceiver which is configured for emitting an NFC signal 608. The emission of the NFC signals 608 enables the NFC detector 606 to receive NFC signals 610 and determine an antenna position.

The determination of the antenna position enables the processor 144 to calculate the connector position 154. For example, the memory 148 may contain the received NFC signals 610. The NFC detector 606 may actually comprise multiple NFC detectors and may enable triangulation of the location of the magnetic resonance imaging antenna 114. Alternatively, the NFC detector 606 may be mounted on the antenna connector 124 and the location of the antenna 114 may be learned by noting how the NFC signals 608 change as the antenna connector 124 is moved along the path 126.

Figure 7:
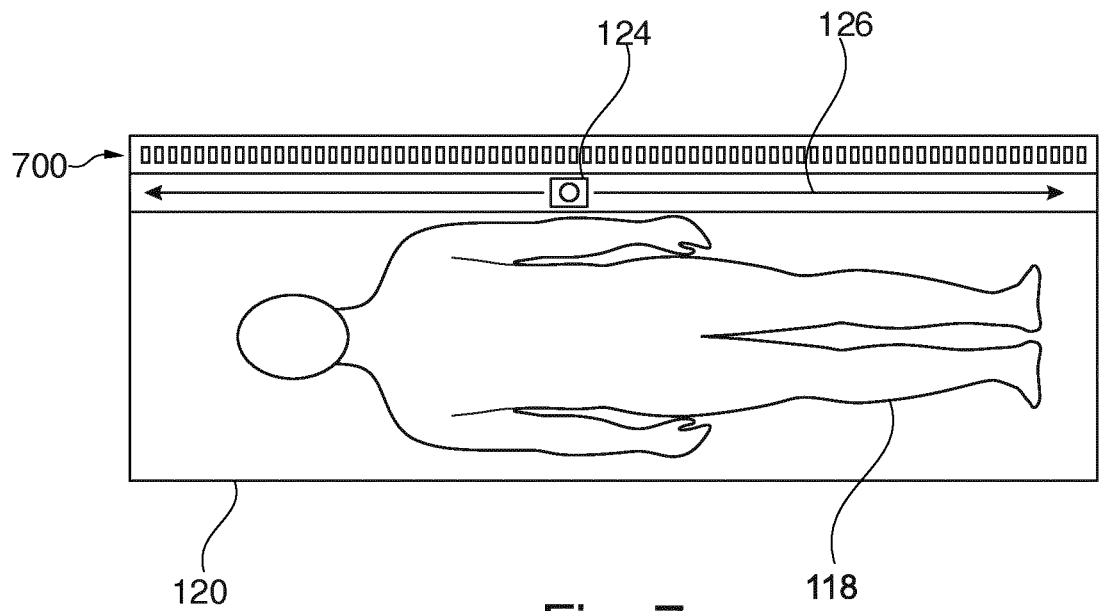
FIG. 7 illustrates an example of a subject support.

FIG. 7 illustrates an example of a subject support 120 that may be integrated into the medical instrument 100 illustrated in FIGS. 1-3. The subject 118 can be shown as reposing on the subject support 120. The antenna connector 124 is visible and is able to travel along the path 126. Parallel to the path 126 is a linear array of buttons 700. An operator can depress one of the buttons and this may be recorded as the connector position 154.

Figure 8:
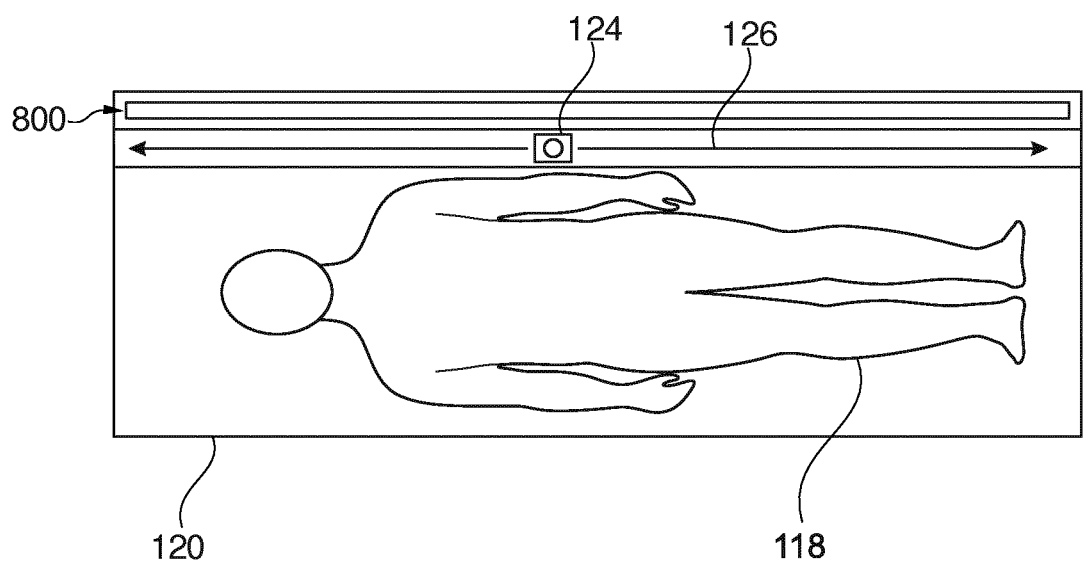
FIG. 8 illustrates a further example of a subject support.

FIG. 8 illustrates a further example of a subject support 120 that may be integrated into the medical instrument 100 of FIGS. 1-3. The example in FIG. 8 is similar to the example in FIG. 7 except the linear array of buttons has been replaced with one or more touch sensors 800. The operator need only touch a position on the touch sensor 800 and this may be registered as the connector position 154.

Figure 9:
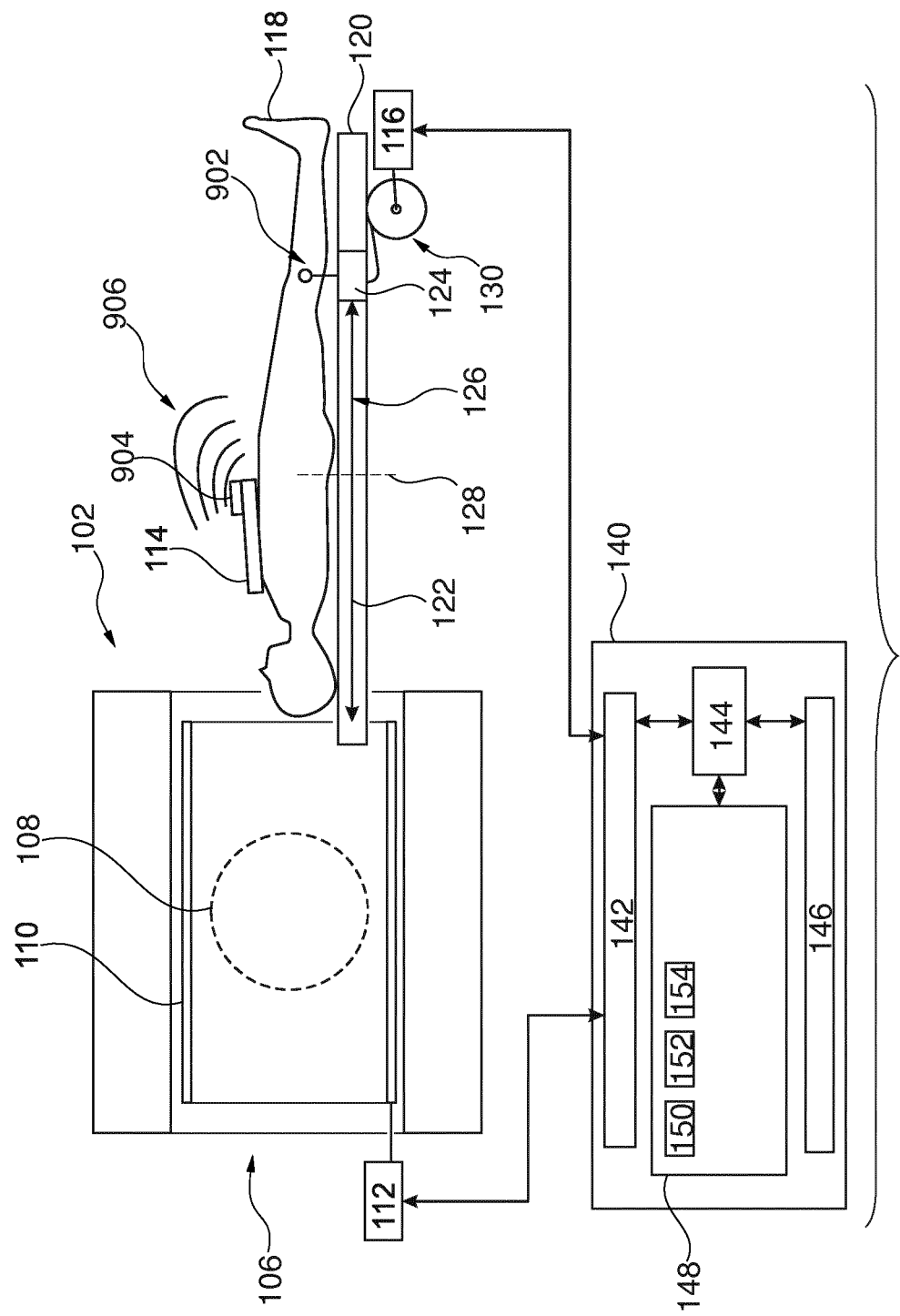
FIG. 9 illustrates a further example of a medical instrument.
Figure 10:
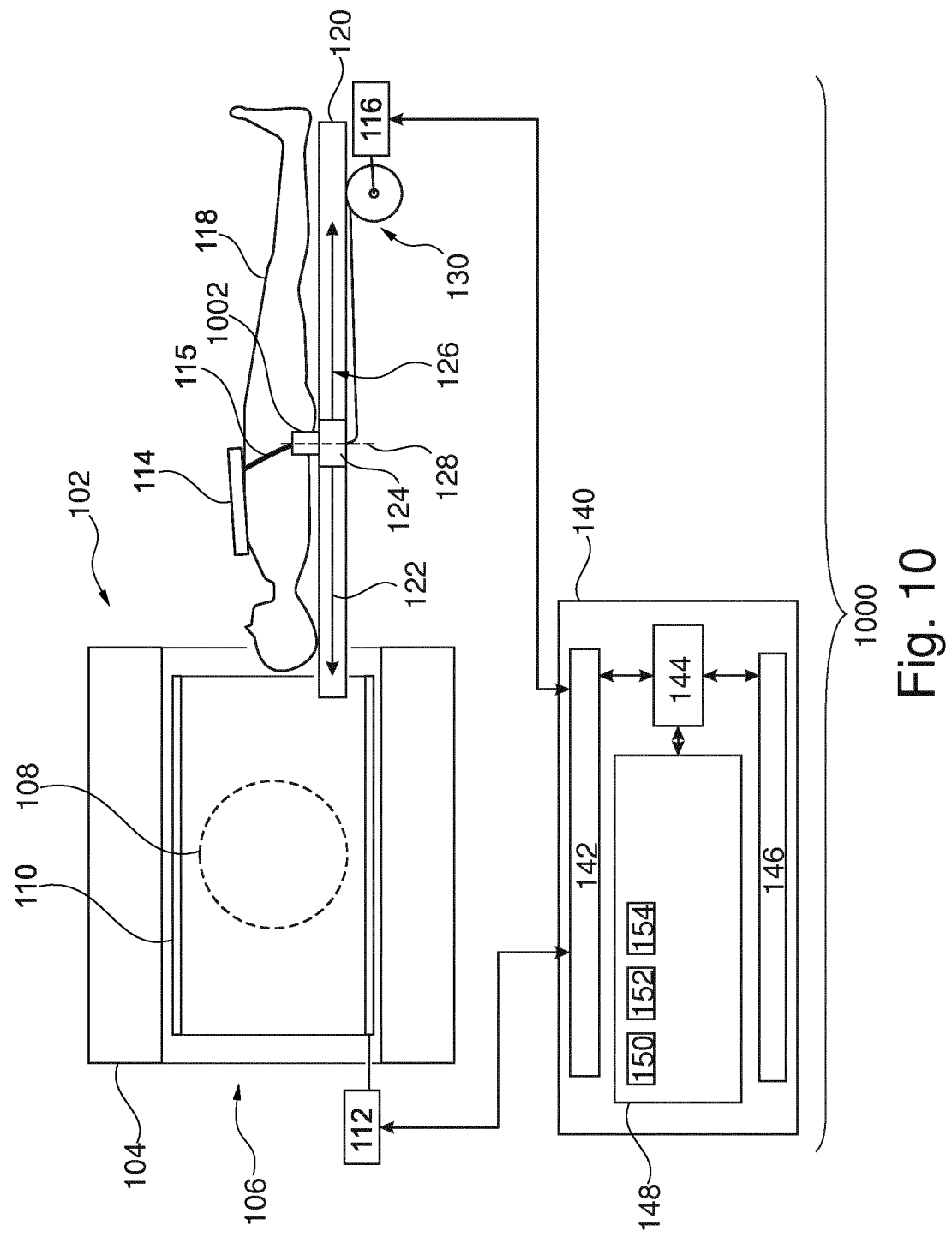
FIG. 10 illustrates a further example of a medical instrument.
Figure 11:
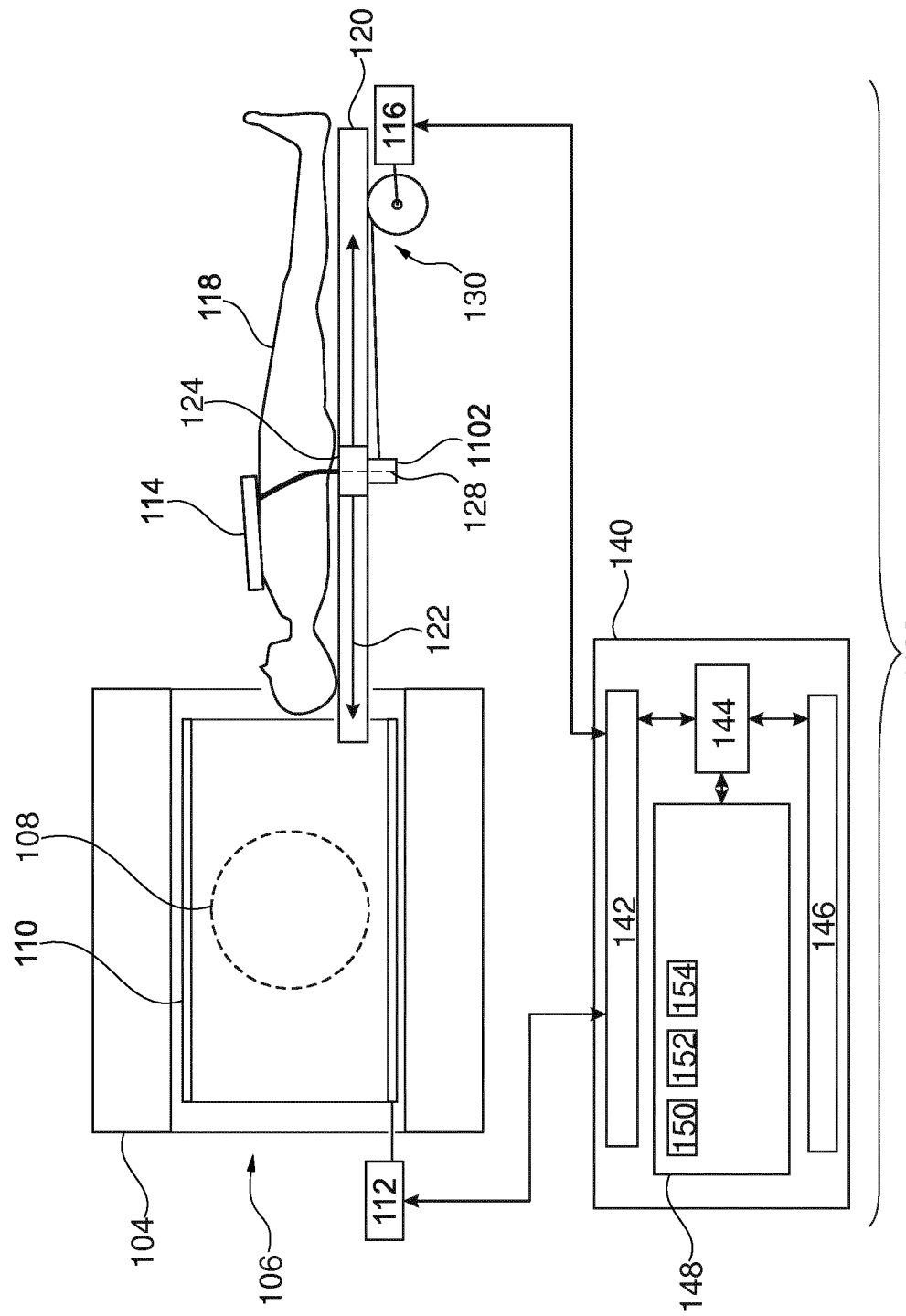
FIG. 11 illustrates a further example of a medical instrument.

FIGS. 9, 10, and 11 illustrate different ways in which the magnetic resonance imaging antenna 114 can connect to the antenna connector 124. FIGS. 9, 10, and 11 do not illustrate how the connector position 154 is determined. FIGS. 9, 10, and 11 can therefore each be combined with FIGS. 1, 2, 3, 4, 5, 6, 7, and 8 to combine different embodiments.

FIG. 9 illustrates a further example of a medical instrument 900. The medical instrument 900 is shown as comprising an RF system transceiver 902 that is integrated into the antenna connector 124. The magnetic resonance imaging antenna 114 is shown as comprising an antenna transceiver 904. The RF system transceiver 902 and the antenna transceiver 904 are configured for forming a wireless connection 906. The magnetic resonance imaging antenna 114 therefore does not have any wired connections during acquisition of magnetic resonance imaging data.

The performance of such a system may depend heavily on the location that the RF system transceiver 902 is positioned. A model can be used to choose the connector position 154 once the location of the magnetic resonance imaging antenna 114 is determined. The location of the magnetic resonance imaging antenna may for example be performed by moving the antenna connector 124 and noting a change in the signal strength of the wireless connection 906 or it may be performed by any one of the means that was illustrated in one of the previous FIGS.

FIG. 10 illustrates a further example of a medical instrument 1000. The medical instrument 1000 is similar to the examples illustrated in FIGS. 1, 2, 3, 4, 5, 6, 7, and 8, except the magnetic resonance imaging antenna 114 has been modified such that the magnetic resonance imaging antenna 114 comprises an antenna plug 1002 at the end of the cable 115. The antenna plug 1002 comprises the coil electronics. The preamplifiers, digitizers and other active components have been moved off of the magnetic resonance imaging antenna and are placed in the antenna plug 1002. This has the advantage of making the magnetic resonance imaging antenna lighter and more transparent wrt. e.g. radiation. This may be possible because the cable length 115 is kept short. The antenna connector 124 then provides power and a digital connection to the antenna plug 1002. This example may be beneficial because the antenna plug 124 can be designed with a standard interface that can interface with many different magnetic resonance imaging antennas 114.

FIG. 11 shows a further example of a medical instrument 1100. The medical instrument 1100 in FIG. 11 illustrates an antenna connector 124 that contains coil electronics 1102. The coil electronics may include the preamplifier for the magnetic resonance imaging antenna 114 and/or various digitizers and other active electronics. This may enable the magnetic resonance imaging antenna 114 to be lighter and have fewer components on its surface. The features of FIG. 11 may be further combined with the examples illustrated in FIGS. 1, 2, 3, 5, 6, 7, and 8.

Figure 12:
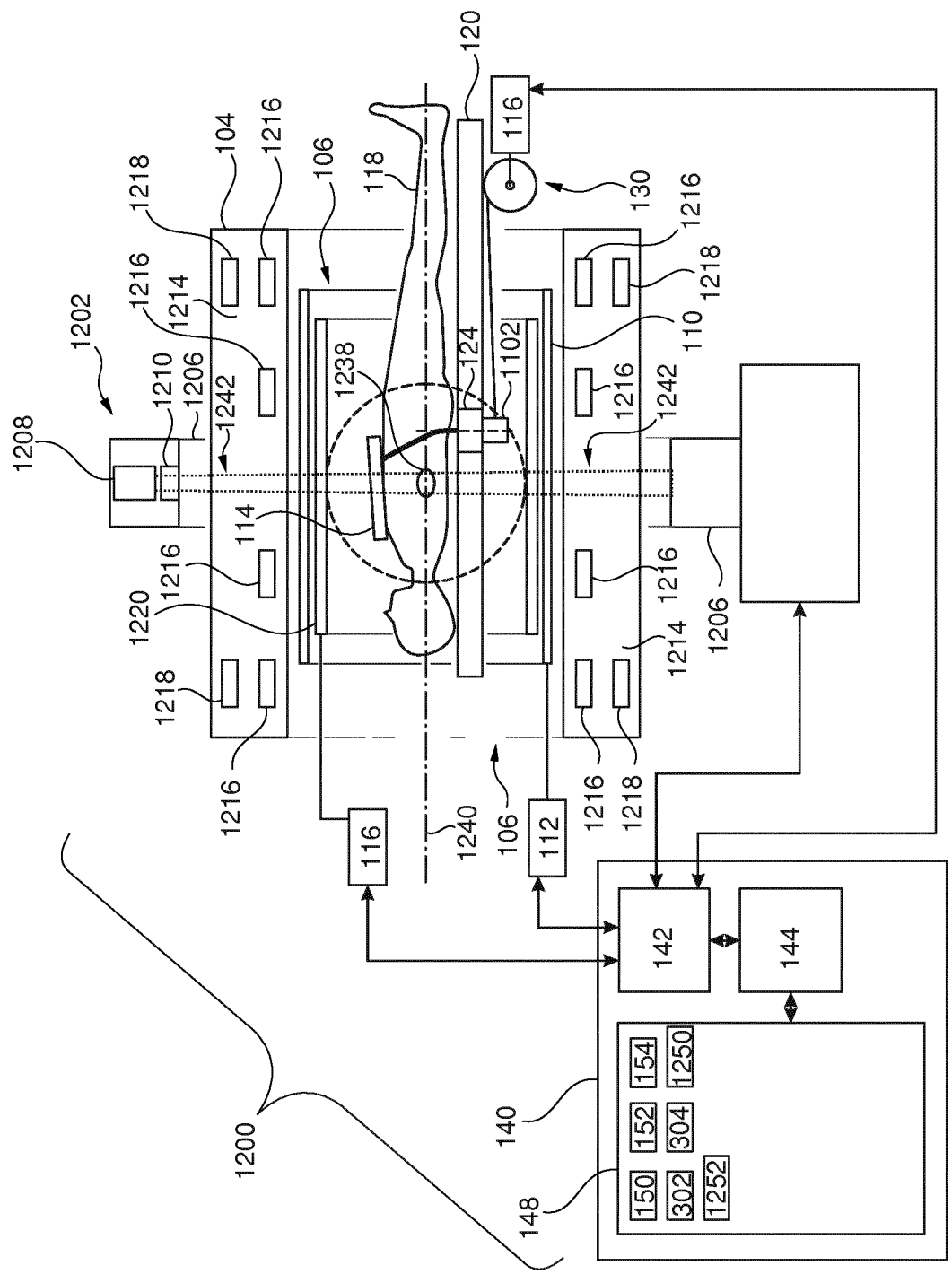
FIG. 12 illustrates a further example of a medical instrument.

FIG. 12 shows a further example of a medical instrument 1200. In this example the medical instrument 1200 further comprises a radiotherapy system 1202. The example shown in FIG. 12 is a combination of the example of FIG. 11 combined with a radiotherapy system 1202. The subject support 120 of FIG. 11 is depicted in FIG. 12.

In this particular example, the radiotherapy system is a linear accelerator (LINAC). However, the depiction of the LINAC is intended to be representative. Other types of radiotherapy systems that can be guided by magnetic resonance imaging may be substituted. The radiotherapy system 1202 comprises a gantry 1206 and a radiotherapy source 1208. The gantry 1206 is for rotating the radiotherapy source 1208 about an axis of gantry rotation 1240. Adjacent to the radiotherapy source 1208 is a collimator 1210.

The magnet 104 shown in this embodiment is a standard cylindrical superconducting magnet. The magnet 1045 has a cryostat 1214 with superconducting coils within it 1216. There are also superconducting shield coils 1218 within the cryostat also. The magnet 104 has a bore 106.

Within the bore 106 of the magnet 104, the subject support 120 supports the subject 118. The subject support 134 may be positioned by a mechanical positioning system. Within the subject 118 there is a target zone 1238. The axis of gantry rotation 1240 is coaxial in this particular embodiment with the cylindrical axis of the magnet 104. The subject support 120 has been positioned such that the target zone 1238 lies on the axis 1240 of the gantry's rotation. The radiation source 1208 is shown as generating a radiation beam 1242 which passes through the collimator 1210 and through the target zone 1238. As the radiation source 1208 is rotated about the axis 1240 the target zone 1238 will always be targeted by the radiation beam 1242. The radiation beam 1242 passes through the cryostat 1214 of the magnet 104. The magnetic field gradient coil 110 may have a gap which separate the magnetic field gradient coil into two sections. If present, this gap reduces attenuation of the radiation beam 1242 by the magnetic field gradient coil 110.

It can be seen that within the bore 116 of the magnet 104 there is an optional body coil 1220 connected to the radio frequency system 116. The radio therapy system 1202 is shown as additionally be connected to the hardware interface 142.

The computer memory 150 is shown as containing machine-executable instructions 152 which enable the processor 148 to control the operation and function of the various components of the medical instrument 100. The computer memory 150 is further shown as containing pulse sequence commands 154, which enable the processor 148 to control the magnetic resonance imaging system 104 to acquire magnetic resonance data. The memory 148 is further shown as containing radio therapy instructions 1250. The radiotherapy instructions 1250 can be used to determine a calculated beam path 1252. The calculated beam path 1252 can be used to modify the vector position 154. It can be seen in FIG. 12 that the antenna connector 124 is safely out of the beam path 1242. By presetting a connector position 154 and then modifying it with the calculated beam path 1252 the quality of the radiotherapy may be improved.

The computer memory 148 is further shown as containing the magnetic resonance image 304 that was reconstructed from the magnetic resonance data 302. The magnetic resonance image 304 may for example be used to guide radiotherapy using the radiotherapy system 1202.

Figure 13:
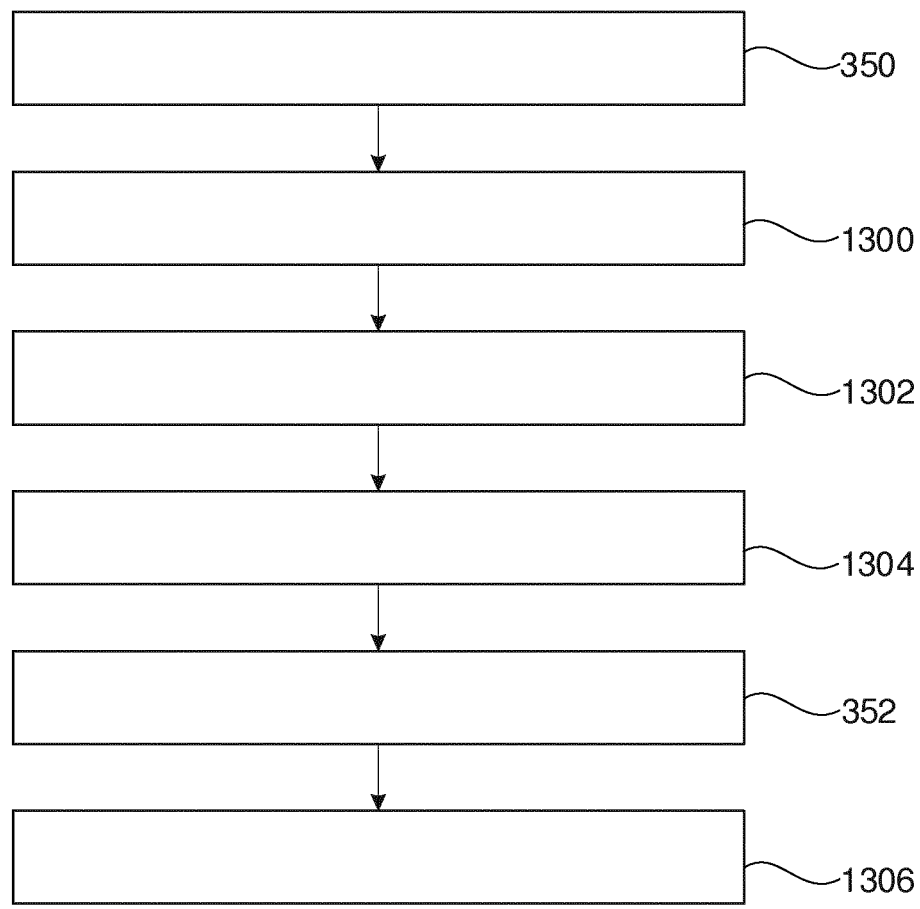
FIG. 13 shows a flow chart which illustrates a method of operating the medical instrument of FIG. 11.

FIG. 13 shows a flowchart which illustrates a method of operating the medical instrument 1200 of FIG. 12. First in step 350 the connector position 154 is received. Next in step 1300 the radiotherapy instructions 1250 are received. Then in step 1302, a beam path 1252 is determined. Next in step 1304, the connector position 154 is modified to avoid the beam path 1252. Then in step 352, the remotely controllable actuator is controlled to move the antenna connector 124 along the path to the connector position 154. Finally, in step 1306, the radiotherapy system 1202 is controlled with the radiotherapy instructions 1250 to irradiate the target zone 1238 using the radiotherapy system 1202. It is not shown in FIG. 13 but also the magnetic resonance imaging data 302 can be acquired and used to create a magnetic resonance image 304 which may be used for guiding the radiotherapy.

In typical MR system setups, RF coils are connected with a RF/supply cable via a connector to the RF interface of the MR scanner. The connection points for RF coils are at fixed on the patient bed. Due to the limited length of the coil cable, the freedom in positioning of the RF coil is limited and not optimal for the clinical workflow. The RF cables of the coils are short for reasons of RF safety.

Fully wireless RF coils would allow free positioning of the RF coils. A lot of digital hardware and power transmission or batteries would need to be additionally integrated in this case, which makes the coils thick and relatively heavy. Examples may provide for lightweight coils that are thin and have more freedom in positioning. In clinical situation is may be beneficial to have thin and lightweight RF coils, which can be positioned freely.

Examples may do away with long cables and constraints of fixed connectors at the end of the cable bed. Moreover, it may increase safety by avoiding long cables.

Examples may use a travelling connector (antenna connector), which use an RF safe cable management integrated in the patient bed/support. The proposed system consists of a dedicated connector travelling along the patient bed.

When the coil is positioned on the patient, a relatively short cable is connected to the moving plug.

In some examples, the plug may be automatically moved via a optical/NFC detection to the corresponding coil.

Examples may allow for more freedom for the connection of the RF coil and increases RF-safety.

Figure 14:
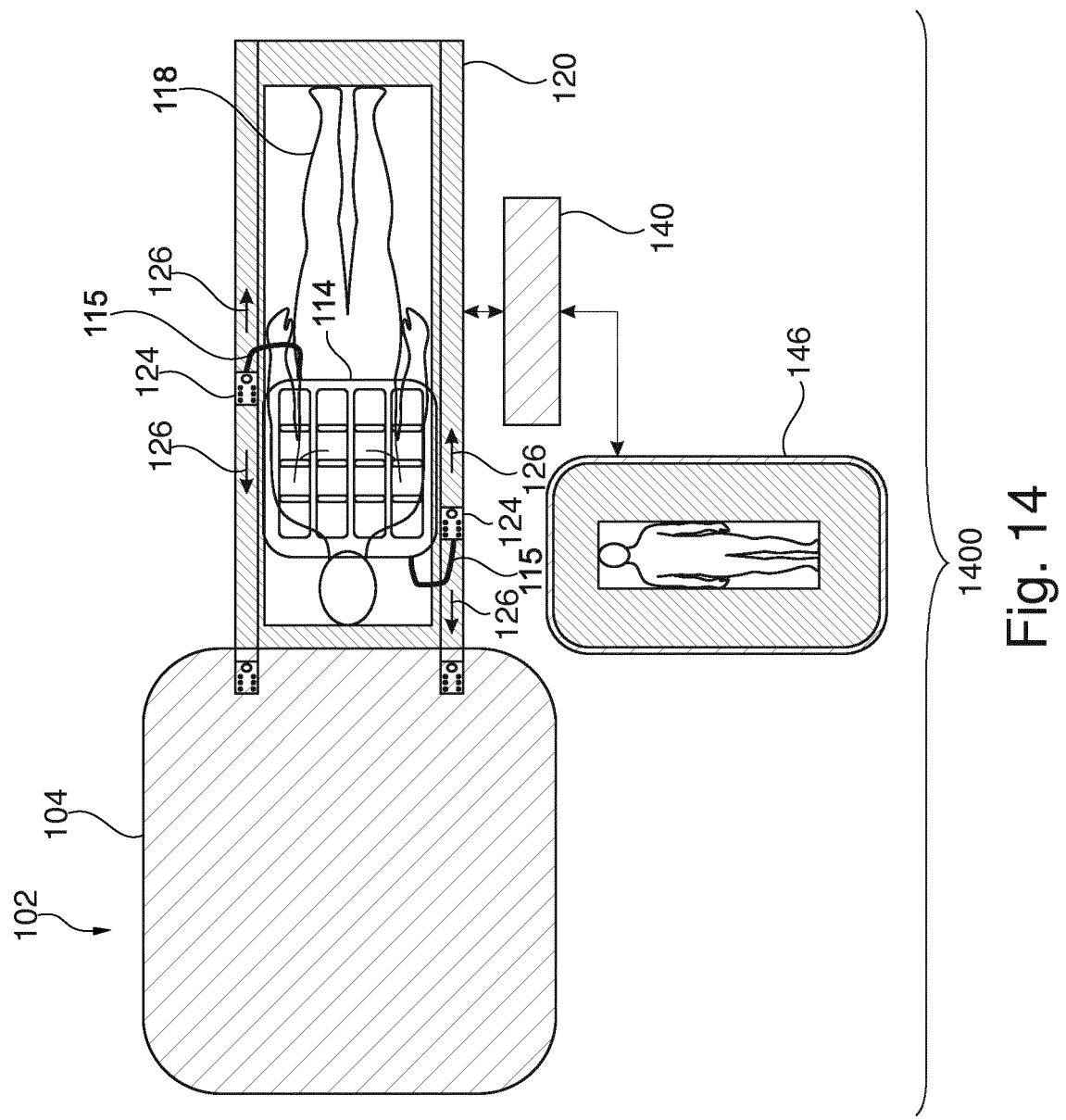
FIG. 14 illustrates a further example of a medical instrument.

FIG. 14 illustrates a further example of a medical instrument 1400. The medical instrument is shown as having an MRI system 102 that has a magnet 104 and a subject support 120. A subject 118 is shown as reposing on the subject support 120. There is a magnetic resonance imaging antenna 114 that has two cables 115 connecting to an antenna connector 124. Both antenna connectors 124 are able to move on paths 126 on either side of the subject 118. The system is controlled by a computer system 140 and there is an app on a user interface 146. The computer system 140 provides processor and control functionality.

FIG. 14 shows a possible example medical instrument: moving plugs are located right and left of the patient bed and travels along a sliding rail system. The travelling plug/connector is electrically connected to a flexible cable located in/under the patient bed. The traveler interface (user interface) 146 can also be wireless/optical connection.

The travelling connectors may move on a sliding system. Flexible connecting cables are integrated in the patient bed/support. The flexible cable can be an optical cable, thus no RF traps are required.

A different embodiment is a wireless connecting traveler plug (antenna connector). Here the coil is connected, but the travelling connector contains a wireless transceiver device, so only a supply cable is required.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical imaging system
102 magnetic resonance imaging system
104 magnet 106 bore of magnet
108 imaging zone
110 magnetic field gradient coils
112 magnetic field gradient coil power supply
114 magnetic resonance imaging antenna
115 cable
116 transceiver
118 subject
120 subject support
122 remotely controllably actuator
124 antenna connector
126 path
128 physical location of connector position
130 cable management system
140 computer system
142 hardware interface
144 processor
146 user interface
148 computer memory
150 machine executable instructions
152 pulse sequence commands
154 connector position
300 region of interest
302 magnetic resonance imaging data
304 magnetic resonance image
350 receive a connector position
352 control the remotely controllable actuator to move the antenna connector along the path to the connector position
400 camera system
402 camera image
404 antenna location model
406 registration of antenna location model to camera image
500 subject model
502 registration of subject model to camera image
504 MRI region of interest selection
600 medical instrument
606 NFC detector
608 NFC signals
610 received NFC signals
700 linear array of buttons
800 touch sensor
900 medical imaging system
902 RF system transceiver
904 antenna transceiver
906 wireless connection
1000 medical instrument
1002 antenna plug with coil electronics
1100 medical instrument
1102 coil electronics
1200 medical instrument
1202 external beam radiotherapy system
1206 gantry
1208 radiotherapy source
1210 collimator
1214 cryostat
1216 superconducting coil
1218 superconducting shield coil
1220 body coil
1238 target zone
1240 axis of gantry rotation
1242 radiation beam path
1250 radiotherapy instructions
1252 calculated beam path
1300 receive radiotherapy instructions configured for controlling the radiotherapy system to irradiate the target zone
1302 determine a beam path using the radiotherapy instructions
1304 modify the connector position to avoid the beam path
1306 control the radiotherapy system to irradiate the target zone using the radiotherapy instructions
1400 medical instrument

The invention claimed is:

1. An apparatus comprising a magnetic resonance imaging system, wherein the apparatus comprises:
a radio frequency system configured for sending and receiving radio frequency signals to acquire magnetic resonance imaging data, wherein the radio frequency system is configured for connecting to a magnetic resonance imaging antenna;
a subject support configured for supporting at least a portion of a subject in an imaging zone of the magnetic resonance imaging system, wherein the subject support comprises an antenna connector configured for connecting to the magnetic resonance imaging antenna, wherein the radio frequency system is configured for connecting to the magnetic resonance imaging antenna via the antenna connector, wherein the subject support comprises a controllable actuator configured for translating the antenna connector along a path to a physical location of a connection position, wherein the connection position is a position for connecting the antenna connector to the radio frequency system;
a camera configured to provide a camera image, wherein the camera image includes an image of at least a portion of the subject support;
a memory comprising machine executable instructions;
a processor for controlling the magnetic resonance imaging system, wherein execution of the machine executable instructions causes the processor to:
ascertain the connection position using the camera image; and
control the controllable actuator to move the antenna connector along the path to the physical location of the connection position.

2. The apparatus of claim 1, wherein the subject support comprises a near field communication (NFC) detector configured for receiving an NFC signal from the magnetic resonance imaging antenna, and wherein execution of the machine executable instructions further causes the processor to ascertain the connection position at least partially using the NFC signal.

3. The apparatus of claim 1, wherein the processor is configured for registering an antenna location model to the camera image, wherein the ascertaining of the connection position using the camera image is at least partially performed using the registration of the antenna location model.

4. The apparatus of claim 1, wherein processor is configured for registering a subject model to the camera image, wherein the ascertaining of the connection position using the camera image is at least partially performed using the registration of the subject model.

5. The apparatus of claim 4, wherein execution of the machine executable instructions further causes the processor to receive an MRI region of interest selection, wherein the connection position is at least partially ascertained using the MRI region of interest selection and the registration of the subject model.

6. The apparatus of claim 1, wherein the subject support further comprises a linear position selector distributed along the path, wherein execution of the machine executable instructions further causes the processor to receive a selected location from the linear position selector, wherein the connection position is at least partially ascertained using the selected location, and wherein the linear position selector is any one of the following: a linear array of buttons or a touch sensor.

7. The apparatus of claim 1, wherein the apparatus further comprises a radiotherapy system, wherein the radiotherapy system is configured for irradiating a target zone, wherein the target zone is within the imaging zone, wherein execution of the machine executable instructions further causes the processor to:
receive radiotherapy instructions configured for controlling the radiotherapy system to irradiate the target zone;
determine a beam path using the radiotherapy instructions;
modify the connection position to avoid the beam path; and
control the radiotherapy system to irradiate the target zone using the radiotherapy instructions.

8. The apparatus of claim 1, wherein the apparatus comprises the magnetic resonance imaging antenna.

9. The apparatus of claim 8, wherein the magnetic resonance imaging antenna comprises a radio frequency cable with an antenna plug, wherein the antenna plug is configured for coupling with the antenna connector, wherein the antenna plug comprises any of the following: an MRI antenna preamplifier, an MRI antenna preamplifier, a digital to analog converter, an analog to digital converter, or combinations thereof.

10. The apparatus of claim 1, wherein the radio frequency system comprises coil electronics within the subject support, wherein the coil electronics are configured to move with the antenna connector, wherein the coil electronics comprise any of the following: an MRI antenna preamplifier, a digital to analog converter, an analog to digital converter, or combinations thereof.

11. The apparatus of claim 1, wherein the antenna connector comprises a radio frequency system transceiver configured for forming a wireless connection with the magnetic resonance imaging antenna, wherein execution of the machine executable instructions further causes the processor to:
ascertain a location of the magnetic resonance imaging antenna at least partially using the RF system transceiver; and
ascertain the connection location using the location of the magnetic resonance imaging antenna.

12. The apparatus of claim 11, wherein the apparatus further comprises the magnetic resonance imaging antenna, wherein the magnetic resonance imaging antenna further comprises an antenna transceiver configured for forming the wireless connection with the RF system transceiver.

13. The apparatus of claim 1, wherein the controllable actuator is a remotely controllable actuator.

14. A method of operating an apparatus, wherein the apparatus comprises a magnetic resonance imaging system and a radio frequency system, wherein the magnetic resonance imaging system is configured for acquiring magnetic resonance imaging data from an imaging zone of the magnetic resonance imaging system, wherein the radio frequency system is configured for sending and receiving radio frequency signals to acquire the magnetic resonance imaging data, and wherein the radio frequency system is configured for connecting to a magnetic resonance imaging antenna,
wherein the apparatus further comprises a subject support configured for supporting at least a portion of a subject in the imaging zone, wherein the subject support comprises an antenna connector configured for connecting to the magnetic resonance imaging antenna, wherein the radio frequency system is configured for connecting to the magnetic resonance imaging antenna via the antenna connector, wherein the subject support comprises a remotely controllable actuator configured for translating the antenna connector along a path to a physical location of a connection position, wherein the connection position is a position for connecting the antenna connector to the radio frequency system,
the method comprises:
capturing a camera image from a camera, wherein the camera image includes an image of at least a portion of the subject support;
ascertaining the connection position using the camera image; and
controlling the remotely controllable actuator to move the antenna connector along the path to the physical location of the connection position.

15. The method of claim 14, further comprising registering an antenna location model to the camera image, wherein the ascertaining of the connection position using the camera image is at least partially performed using the registration of the antenna location model.

16. The method of claim 14, further comprising registering a subject model to the camera image, wherein the ascertaining of the connection position using the camera image is at least partially performed using the registration of the subject model.

17. The method of claim 16, further comprising receiving an MRI region of interest selection, wherein the connection position is at least partially ascertained using the MRI region of interest selection and the registration of the subject model.

18. The method of claim 14, wherein the subject support further comprises a linear position selector distributed along the path, wherein the method further comprises:
receiving a selected location from the linear position selector; and
ascertaining the connection position at least partially using the selected location, and wherein the linear position selector is any one of the following: a linear array of buttons or a touch sensor.

19. A non-transitory computer readable storage medium having stored thereon machine executable instructions configured for execution by a processor to control an apparatus, wherein the apparatus comprises a magnetic resonance imaging system, wherein the apparatus further comprises a radio frequency system configured for acquiring magnetic resonance imaging data from an imaging zone of the magnetic resonance imaging system, wherein the radio frequency system is configured for sending and receiving radio frequency signals to acquire the magnetic resonance imaging data, wherein the radio frequency system is configured for connecting to a magnetic resonance imaging antenna, wherein the apparatus further comprises:
a subject support configured for supporting at least a portion of a subject in the imaging zone; and
a camera configured to provide a camera image, wherein the camera image includes an image of at least a portion of the subject support, wherein the subject support comprises an antenna connector configured for connecting to the magnetic resonance imaging antenna, wherein the radiofrequency system is configured for connecting to the magnetic resonance imaging antenna via the antenna connector, wherein the subject support comprises a remotely controllable actuator configured for translating the antenna connector along a path to a physical location of a connection position, wherein the connection position is a position for connecting the antenna connector to the radio frequency system, wherein execution of the machine executable instructions causes the processor to: acquire the camera image from the camera;

ascertain the connection position using the camera image; and control the remotely controllable actuator to move the antenna connector along the path to the physical location of the connection position.

* * * * *